United States Patent [19]
Kohn et al.

[11] Patent Number: 6,048,899
[45] Date of Patent: Apr. 11, 2000

[54] ANTICONVULSANT ENANTIOMERIC AMINO ACID DERIVATIVES

[75] Inventors: Harold Kohn; Shridhar V. Andurkar, both of Houston, Tex.

[73] Assignee: Research Corporation Tech., Inc., Tucson, Ariz.

[21] Appl. No.: 09/107,206

[22] Filed: Jun. 29, 1998

Related U.S. Application Data

[63] Continuation-in-part of application No. 08/818,688, Mar. 17, 1997, Pat. No. 5,773,475.

[51] Int. Cl.[7] .................... A61K 31/16; A61K 31/165; C07C 235/06; C07C 233/05
[52] U.S. Cl. ..................... 514/626; 564/194; 564/196
[58] Field of Search ................... 564/194, 196; 514/626

[56] References Cited

U.S. PATENT DOCUMENTS

| | | | |
|---|---|---|---|
| 5,153,226 | 10/1992 | Chucholowski et al. | 514/617 |
| 5,378,729 | 1/1995 | Kohn et al. | 514/231.2 |
| 5,654,301 | 8/1997 | Kohn et al. | 514/231.2 |
| 5,814,669 | 9/1998 | Stelzer et al. | 514/626 |

FOREIGN PATENT DOCUMENTS 0 194 464   9/1986   European Pat. Off. .

OTHER PUBLICATIONS

Kohn, Harold et al. "Preparation and anticonvulsant activity of a series of functionalized. alpha.—heteroatom–substituted amino acids", *J. Med. Chem.*, 1991, 34, 2444–2452.

Kohn, Harold et al. "Marked stereospecificity in a new class of anticonvulsants", *Chemical Abstracts*, 1988, 109, Abstract No. 183045.

Choi, Daeock et al. "Synthesis and Anticonvulsant Activities of N–Benzyl–2–acetamidopropionamide Derivatives", *J. Med. Chem.*, 1996, 39, 1907–1916.

*Primary Examiner*—Shailendra Kumar
*Attorney, Agent, or Firm*—Scully, Scott, Murphy & Presser

[57] ABSTRACT

The present invention is directed to N-benzyl-2-amino-3-methoxypropionamide and stereoisomers the use thereof anti-convulsant and an intermediate in the preparation of other anti-convulsants.

19 Claims, No Drawings

ANTICONVULSANT ENANTIOMERIC AMINO ACID DERIVATIVES

RELATED APPLICATIONS

This application is a continuation-in-part of application U.S. Ser. No. 08/818,688 filed Mar. 17, 1997, now U.S. Pat. No. 5,773,475.

FIELD OF THE INVENTION

The present invention relates to novel enantiomeric compounds and pharmaceutical compositions useful in the treatment of epilepsy and other CNS disorders.

BACKGROUND OF THE INVENTION

The predominant application of anticonvulsant drugs is the control and prevention of seizures associated with epilepsy or related central nervous system disorders. Epilepsy refers to many types of recurrent seizures produced by paroxysmal excessive neuronal discharges in the brain; the two main generalized seizures are petit mal, which is associated with myoclonic jerks, akinetic seizures, transient loss of consciousness, but without convulsion; and grand mal which manifests in a continuous series of seizures and convulsions with loss of consciousness.

The mainstay of treatment for such disorders has been the long-term and consistent administration of anticonvulsant drugs. Most drugs in use are weak acids that, presumably, exert their action on neurons, glial cells or both of the central nervous system. The majority of these compounds are characterized by the presence of at least one amide unit and one or more benzene rings that are present as a phenyl group or part of a cyclic system.

Much attention has been focused upon the development of anticonvulsant drugs and today many such drugs are well known. For example, the hydantoins, such as phenytoin, are useful in the control of generalized seizures and all forms of partial seizures. The oxazolidinediones, such as trimethadione and paramethadione, are used in the treatment of nonconvulsive seizures. Phenacemide, a phenylacetylurea, is one of the most well known anticonvulsants employed today, while much attention has recently been dedicated to the investigation of the diazepines and piperazines. For example, U.S. Pat. Nos. 4,002,764 and 4,178,378 to Allgeier, et al. disclose esterified diazepine derivatives useful in the treatment of epilepsy and other nervous disorders. U.S. Pat. No. 3,887,543 to Nakanishi, et al. describes a thieno [2,3-e] [1,4]diazepine compound also having anticonvulsant activity and other depressant activity. U.S. Pat. No. 4,209,516 to Heckendorn, et al. relates to triazole derivatives which exhibit anticonvulsant activity and are useful in the treatment of epilepsy and conditions of tension and agitation. U.S. Pat. No. 4,372,974 to Fish, et al. discloses a pharmaceutical formulation containing an aliphatic amino acid compound in which the carboxylic acid and primary amine are separated by three or four units. Administration of these compounds in an acid pH range are useful in the treatment of convulsion disorders and also possess anxiolytic and sedative properties.

U.S. Pat. No. 5,378,729 to Kohn, et al. discloses compounds and pharmaceutical compositions having central nervous system (CNS) activity which are useful in the treatment of epilepsy and other CNS disorders having the following general formula:

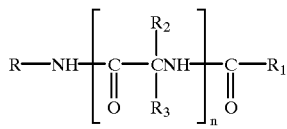

wherein

R is hydrogen, lower alkyl, lower alkenyl, lower alkynyl, aryl, aryl lower alkyl, heterocyclic, heterocyclic lower alkyl, lower alkyl heterocyclic, lower cycloalkyl, lower cycloalkyl lower alkyl, and R is unsubstituted or is substituted with at least one electron withdrawing group, or electron donating group.

$R_1$ is hydrogen, lower alkyl, lower alkenyl, lower alkynyl, aryl lower alkyl, aryl, heterocyclic lower alkyl, heterocyclic, lower cycloalkyl, lower cycloalkyl lower alkyl, each unsubstituted or substituted with an electron donating group or an electron withdrawing group and $R_2$ and $R_3$ are independently hydrogen, lower alkyl, lower alkenyl, lower alkynyl, aryl lower alkyl, aryl, heterocyclic, heterocyclic lower alkyl, lower alkyl heterocyclic, lower cycloalkyl, lower cycloalkyl lower alkyl, or Z-Y wherein $R_2$ and $R_3$ may be unsubstituted or substituted with at least one electron withdrawing group or electron donating group;

Z is O, S, S $(O)_a$, $NR_4$, $PR_4$ or a chemical bond;

Y is hydrogen, lower alkyl, aryl, aryl lower alkyl, lower alkenyl, lower alkynyl, halo, heterocyclic, or heterocyclic lower alkyl, and Y may be unsubstituted or substituted with an electron donating group or an electron withdrawing group, provided that when Y is halo, Z is a chemical bond, or ZY taken together is $NR_4NR_5R_7$, $NR_4OR_5$, $ONR_4R_7$, $OPR_4R_5$, $PR_4OR_5$, $SNR_4R_7$, $NR_4SR_7$, $SPR_4R_5$, $PR_4SR_7$, $NR_4PR_5R_6$, $PR_4NR_5R_7$,

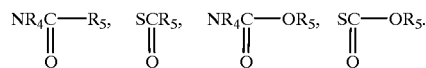

$R_4$, $R_5$ and $R_6$ are independently hydrogen, lower alkyl, aryl, aryl lower alkyl, lower alkenyl, or lower alkynyl, wherein $R_4$, $R_5$ and $R_6$ may be unsubstituted or substituted with an electron withdrawing group or an electron donating group, $R_7$ is $R_6$, $COOR_8$ or $COR_8$, $R_8$ is hydrogen, lower alkyl, or aryl lower alkyl, and the aryl or alkyl group may be unsubstituted or substituted with an electron withdrawing group or an electron donating group and n is 1–4 and a is 1–3.

Recently, Geurts, et al. in *J. Med. Chem.*, 1998, 41, 24–30 disclosed that N-benzyloxycarbonyl glycine and N-(benzyloxycarbonyl) glycine, enzylamide exhibited anticonvulsant activity as measured in the maximal electroshock test (MES).

Unfortunately, despite the many available pharmacotherapeutic agents, and potential candidates for same, a significant percentage of the population with epilepsy or related disorders are poorly managed. Moreover, none of the drugs presently available are capable of achieving total seizure control, Research is continuing in this area to find better and more effective anticonvulsant agents.

The present inventors have found a novel compound that exhibits anti-convulsant activity and is useful as a drug for treating CNS disorders.

SUMMARY OF THE INVENTION

Accordingly, the present invention is directed to a N-benzyl-2-amino-3-methoxypropionamide of the formula:

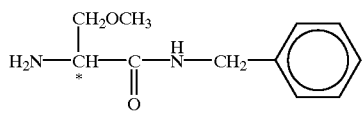

I or pharmaceutically acceptable salts thereof. It is preferably directed to the R-stereoisomer thereof. The compound of Formula I is useful as an intermediate in preparing N-benzyl-2-acetamido propionamide derivatives especially those in the R configuration having the formula:

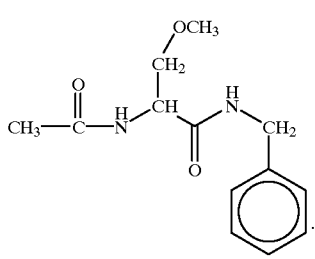

II

Compounds of Formula II exhibit anti-convulsant activity, as described in copending application U.S. Ser. No. 08/818,688, the contents of which are incorporated by reference.

The compound of Formula I is also useful as an anticonvulsant.

The present invention also contemplates employing the compound of Formula I in a pharmaceutical composition. Moreover, the administration of an effective amount of the compound of Formula I in its pharmaceutically acceptable forms provides an excellent regime for the treatment of epilepsy, nervous anxiety, psychosis, insomnia, and other related central nervous disorders.

DETAILED DESCRIPTION OF THE INVENTION

The present invention is directed to N-benzyl-2-amino-3-methoxypropionamide. As indicated hereinabove, this compound has two utilities, one as an intermediate in the preparation of other anticonvulsants. It is also useful for treating central nervous disorders in mammals, such as man, dogs, cats, horses, pigs, cows and the like. When used as a therapeutic, it is preferred that the compound of the present invention be substantially pure, i.e., substantially free from impurities. It is most preferred that the compound of the present invention be at least 75% pure (w/w) and more preferably greater than about 90% pure (w/w) and most preferably greater than about 95% pure (w/w).

The compound of the present invention contains one asymmetric carbon. This asymmetric carbon is indicated in the compound of Formula I by an asterisk. The stereochemistry of the asymmetric carbon at the asterisk is preferably in the R configuration.

When present as the R isomer, it is especially preferred that the compound of the present invention be substantially enantiomerically pure, i.e., substantially free from the corresponding S isomer. Most preferably, in this embodiment, the compound of the present invention contains at least about 75% (w/w) R stereoisomer, and more preferably greater than about 85% (w/w) R stereoisomer, and even more preferably greater than about 90% (w/w) R stereoisomer, and especially most preferably greater than about 95% R stereoisomer (w/w). Thus, this preferred embodiment of the present invention contemplates compounds having at most about 20% S isomer (w/w), and even more preferably less than about 10% S isomer (w/w), and most preferably less than about 5% S isomer (w/w). Thus, it is preferred in this embodiment that the product be at least about 65% enantiomerically pure, more preferably at least about 75% enantiomerically pure and even more preferably at least about 85% enantiomerically pure and most preferably at least about 95% enantiomerically pure.

The compound of Formula I is prepared by art recognized techniques from commercially available starting materials. As indicated hereinabove, it is an intermediate in the preparation of compounds of Formula II.

An exemplary procedure for preparing the compound of the present invention is outlined hereinbelow in Scheme 1:

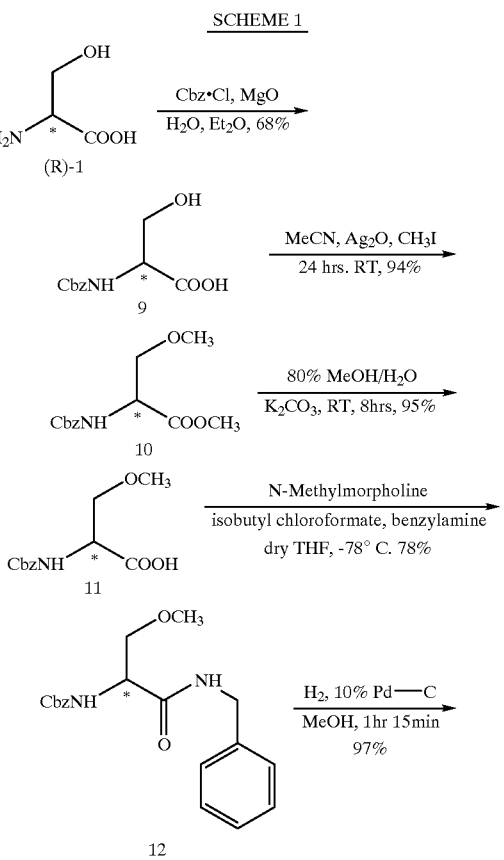

-continued

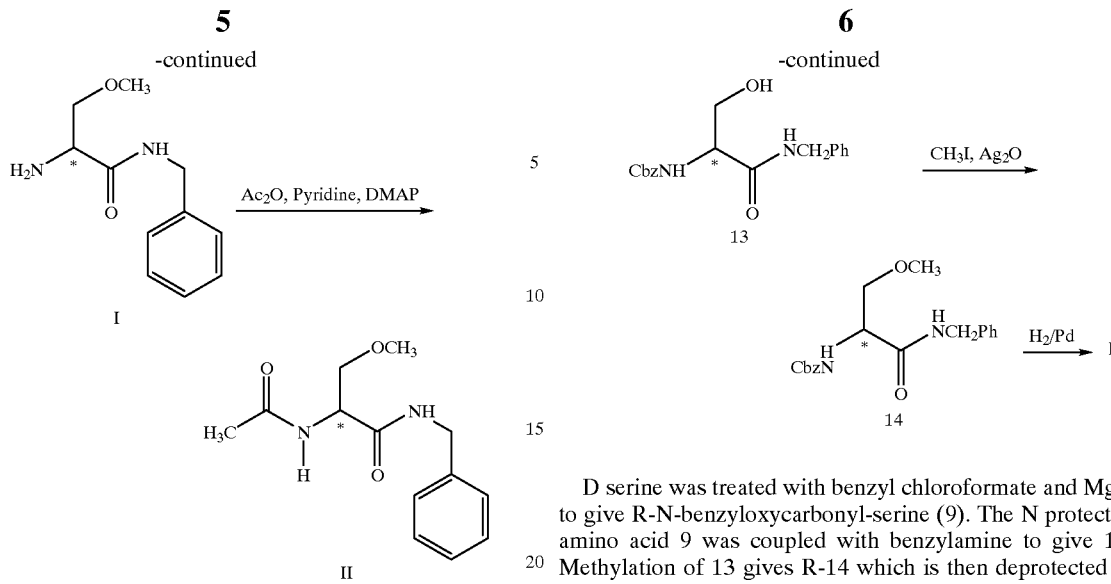

D Serine (1) is protected with a N-protecting group known in the art, by standard techniques. Thus, for example, it is reacted with carbobenzoxy chloride (CBZ-Cl, benzyl chloroformate) generating the (R)-N-benzyloxycarbonylserine 9. The protected serine adduct is converted to the corresponding ether under Williamson conditions by reacting it with methyl iodide or other alkyl halide, wherein alkyl contains preferably 1–6 carbon atoms and halide is preferably chloride, bromide or iodide in the presence of base (e.g., $Ag_2O$) to form an ether 10. Under these conditions, the acid is also esterified. Subsequent hydrolysis of the ester group in 10 permits amide coupling with $ArCH_2NH_2$ using amide coupling methodology (e.g., mixed anhydride 1,1' Carbonyldiimidazole) to give the amide 12. Deprotection of the N-protecting group provides the free amine of the present invention, i.e., the compound of Formula I.

This compound, as indicated hereinabove is an intermediate in the preparation of the compound of Formula II. The compound of Formula II is formed by reacting the compound of Formula I with an acylating agent such as acetic anhydride in base (e.g., pyridine). However, the compound of Formula II is one of the products described in copending application exhibiting anticonvulsant activity, as described in U.S. Ser. No. 08/818,688, the contents which are incorporated by reference.

Alternatively, the compound of Formula I is prepared by the following manner, as illustrated in the following schematic:

SCHEME 2

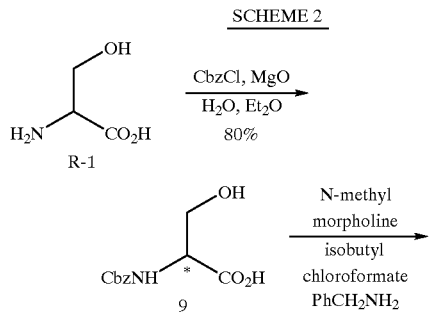

D serine was treated with benzyl chloroformate and MgO to give R-N-benzyloxycarbonyl-serine (9). The N protected amino acid 9 was coupled with benzylamine to give 13. Methylation of 13 gives R-14 which is then deprotected to provide the compound of Formula I in the R configuration. If desired, the compound of Formula II can be prepared in accordance with the procedure of Scheme 2, from the acetylation of the compound of Formula I.

These two methodologies suggest various methodologies for preparing compounds of Formula I. Inasmuch as this compound is the desired product, it can be isolated from the various products and the starting material using classical techniques known in the art, such as chromatography and the like.

If necessary, in any of the procedures described hereinabove, the optical purity of the product of Formula I may be enhanced by further separation of the S enantiomer from the R enantiomer, by standard techniques known in the art, such as chiral chromatography using a standard chiral support known in the art.

Alternatively, in any of the procedures provided hereinabove, a racemic serine may be utilized as the starting material. Utilizing the procedure in the schemes outlined hereinabove would provide the racemic mixture of the various products including the compound of Formula I. Thus, an optically inactive compound of Formula I can be isolated utilizing the scheme described hereinabove which can also be used as in intermediate in the preparation of compounds of Formula II.

Another method of preparing an optically active compound of Formula I would be to prepare the racemic mixture of the compound of Formula I in accordance with the procedure of either Scheme I or II; then the racemic mixture of the compound of Formula I can be resolved into the R isomer and/or S isomer, if desired by standard techniques known in the art, such as chiral chromatography. Moreover, it should be noted that if the S isomer is desired, it can be prepared using the procedure described herein using L-serine as the starting material rather than D-serine.

As described in U.S. Ser. No. 08/818,688, the contents of which are incorporated by reference, the compound of Formula II is useful as an anti-convulsant. Thus, the compound of Formula I is useful as an intermediate in the preparation of an anticonvulsant of Formula II.

Besides acting as an intermediate as depicted in the above scheme, the compound of the present invention also exhibits anti-convulsant activity.

More specifically, the compound of Formula I is useful for the treatment of central nervous disorders, such as epilepsy, nervous anxiety, psychosis, insomnia and the like in animals, e.g., mammals, such as man, in need thereof. It exhibits anti-convulsant activity, and can be administered for short term treatment. Moreover, the compound of the present invention has the added advantage of being useful in drug regimes for long-term treatment. The compound of the present invention is additionally substantially non-toxic exhibiting minimal toxicity to the treated animal. Thus, the compound of Formula I is useful for treating CNS disorders in animals including mammals, and especially humans. It is preferred that the compound of Formula I, when used as a pharmaceutical, be substantially pure, as defined herein.

In a preferred embodiment, the compound of the present invention is either a racemic mixture or enriched in the R stereoisomer form, i.e., the ratio of R stereoisomer to S stereoisomer is $\geq 1$. As indicated hereinabove, the compound of the present invention is enantiomerically pure, as defined herein.

In an even more preferred embodiment, the compound of Formula I is both substantially pure and enantiomerically pure in the R stereoisomer.

The present invention is also directed to pharmaceutical compositions containing the compound of the present invention as well as the use of this compound in treating CNS disorders.

The compound of the present invention is useful as such as depicted in the Formula I or can be employed in the form of salts in view of its basic nature by the presence of the free amino group. Thus, this compound forms salts with a wide variety of acids, inorganic and organic, including pharmaceutically acceptable acids. The salts with therapeutically acceptable acids are of course useful in the preparation of formulation where enhanced water solubility is most advantageous.

These pharmaceutically acceptable salts have also therapeutic efficacy. These salts include salts of monomer acids such as hydrochloric, hydroiodic, hydrobromic, phosphoric, metaphosphoric, nitric acid and sulfuric acids as well as salts of organic acids, such as tartaric, acetic, citric, malic, benzoic, perchloric, glycolic, gluconic, succinic, aryl sulfonic, (e.g., p-toluene sulfonic acids, benzenesulfonic), phosphoric, malonic, and the like.

It is preferred that the compound of the present invention be administered in amounts ranging from about 1 mg to about 100 mg per kilogram of body weight per day. This dosage regimen may be adjusted by the physician to provide the optimum therapeutic response. For example, several divided doses may be administered daily or the dose may be proportionally reduced as indicated by the exigencies of the therapeutic situation. A decided practical advantage is that the compound of the present invention may be administered in a convenient manner, such as by oral, intravenous (where water soluble), intramuscular or subcutaneous routes.

The compound of the present invention may be orally administered, for example, with an inert diluent or with an assimilable edible carrier, or it may be enclosed in hard or soft shell gelatin capsules, or it may be compressed into tablets, or it may be incorporated directly into the food of the diet. For oral therapeutic administration, the active compound may be incorporated with excipients and used in the form of ingestible tablets, buccal tablets, troches, capsules, elixirs, suspensions, syrups, wafers, and the like. Such compositions and preparations should contain at least 1% of active compound. The percentage of the compositions and preparations may, of course, be varied and may conveniently be between about 5 to about 80% of the weight of the unit. The amount of active compound in such therapeutically useful compositions is such that a suitable dosage will be obtained. Preferred compositions or preparations according to the present invention are prepared so that an oral dosage unit form contains between about 10 mg and 6 g of active compound.

The tablets, troches, pills, capsules and the like may also contain the following: A binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavoring such as cherry or orange flavor. Of course, any material used in preparing any dosage unit form should be pharmaceutically pure and substantially non-toxic in the amounts employed. In addition, the active compound may be incorporated into sustained-release preparations and formulations. For example, sustained release dosage forms are contemplated wherein the active ingredient is bound to an ion exchange resin which, optionally, can be coated with a diffusion barrier coating to modify the release properties of the resin.

The active compound may also be administered parenterally or intraperitoneally. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions (where water soluble) or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersions and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filtered sterilization. Generally, dispersions are prepared by incorporating the various sterilized active ingredient into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from previously sterile-filtered solution thereof.

As used herein, "pharmaceutically acceptable carrier" includes any and all solvents, dispersion media, coatings, antibacterial and antifungal agents, isotonic and absorption delaying agents, and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

It is especially advantageous to formulate parenteral compositions in dosage unit form for ease of administration arid uniformity of dosage. Dosage unit form as used herein refers to physically discrete units suited as unitary dosages for the mammalian subjects to be treated; each unit containing a predetermined quantity of active material calculated to produce the desired therapeutic effect in association with the required pharmaceutical carrier. The specifics for the novel dosage unit forms of the invention are dictated by and directly dependent on (a) the unique characteristics of the active material and the particular therapeutic effect to be achieved, and (b) the limitations inherent in the art of compounding such an active material for the treatment of disease in living subjects having a diseased condition in which bodily health is impaired as herein disclosed in detail.

The principal active ingredient is compounded for convenient and effective administration in effective amounts with a suitable pharmaceutically acceptable carrier in dosage unit form as hereinbefore described. A unit dosage form can, for example, contain the principal active compound in amounts ranging from about 10 mg to about 6 g. Expressed in proportions, the active compound is generally present in from about 1 to about 750 mg/ml of carrier. In the case of compositions containing supplementary active ingredients, the dosages are determined by reference to the usual dose and manner of administration of the said ingredients.

Unless indicated to the contrary, percentages are by weight.

For a better understanding of the present invention reference is made to the following description and examples.

EXAMPLE 1

N-BENZYL 2-AMINO-3-METHOXYPROPIONAMIDE (a) ((R)-N-BENZYLOXYCARBONYL)SERINE ((R)-9)

D-Serine (5 g) was dissolved in water (85 mL). To this was added MgO (6 g), and ethyl ether (40 mL). The mixture was cooled in an ice bath to 0° C. To this ice-cold mixture was added slowly, dropwise benzylchloroformate (95%, 11 mL). Upon complete addition, the mixture was stirred at 0° C. (2 h) and then allowed to spontaneously warm to room temperature. Stirring was continued for an additional 30 minutes. The mixture was filtered and the filtrate washed with ethyl ether (2×25 mL). The aqueous layer was separated and cooled in an ice bath to 0° C. The pH of this ice-cold aqueous layer was carefully adjusted to 3.0 using 5 N HCl. The acidified solution was stored in a refrigerator overnight. The white crystalline solid product was isolated by filtration, and dried in vacuo. The filtrate was extracted with ethyl acetate (2×50 mL). The combined ethyl acetate extracts were dried ($Na_2SO_4$), filtered and evaporated in vacuo to obtain additional amounts of the white crystalline product. Total product obtained was 7.51 g (68%): mp 118–120° C.

(b) Enriched R METHYL-42-N-(BENZYLOXYCARBONYL)AMINO 3-METHOXYPROPIONATE (10)

To a solution of 9 (1.72g, 7.21 mmol) in actonitrile (150 mL) was added methyl iodide (10.23 g, 72.1 mmol, 4.5 mL) and silver(I)oxide (8.4 g, 36 mmol) and the mixture was stirred in the dark at room temperature for 24 hours. The insoluble salts and excess silver oxide were removed by filtration and the filtrate was evaporated in vacuo to obtain an oily residue which was subjected to flash column chromatography (silica gel and 5% $MeOH\text{-}CHCl_3$) to obtain 10 as a pale yellow oil (1.81 g, 94%,): $R_f$ (10% $MeOH/CHCl_3$) 0.75. The product obtained was partially racemized, in an approximate 85:15 enantiomeric mixture, of the R and S stereoisomers.

In a slight variation, the above compound was prepared as follows: To a $CH_3CN$ solution (150 mL) of 9 (1.72 g, 7.2 mmol) was added successively $Ag_2O$ (8.40 g, 36 mmol) and MeI (4.5 mL, 72 mmol) and the mixture stirred at room temperature (24 hours). The mixture was filtered and the filtrate evaporated in vacuo to obtain an oily residue which was purified by column chromatography ($SiO_2$, 5% $MeOH$—$CHCl_3$) to obtain pure 10 (1.81 g, 94%) as a clear oil: $[\alpha]^{23}_D$ (c=3.4, MeOH)=+9.5°; $R_f$ 0.75 (10% MeOH—$CHCl_3$); IR (liquid film) 3333, 3033, 2953, 1725, 1520, 1455, 1342, 1298, 1213, 1119, 1064, 978, 915, 776, 741, 699 $cm^{-1}$; $^1H$ NMR ($CDCl_3$) δ3.34 (s, $CH_2OC\underline{H}_3$), 3.62 (dd, J×3.3, 9.3 Hz, $C\underline{H}H'OCH_3$), 3.78 (s, $C(O)OC\underline{H}_3$), 3.84 (dd, J=3.3, 9.3 Hz, $CH\underline{H}'OCH_3$), 4.40–4.46 (m, $C\underline{H}$), 5.14 (s, $PhC\underline{H}_2$), 5.67 (br d, J=8.1 Hz, NH), 7.33–7.40 (m, 5 PhH); $^{13}C$ NMR ($CDCl_3$) 52.8 ($C(O)OCH_3$), 54.5 ($\underline{C}H$), 59.5 ($CH_2O\underline{C}H_3$), 67.2 ($Ph\underline{C}H_2$), 72.5 ($\underline{C}H_2OCH_3$), 128.3 ($2\underline{C}_2$' or $2\underline{C}_3$'), 128.4 ($\underline{C}_4$'), 128.7 ($2\underline{C}_2$' or $2\underline{C}_3$'), 136.4 ($\underline{C}_1$'), 156.2 ($\underline{C}(O)NH$), 171.0 ($\underline{C}(O)O$) ppm; MS (+CI) (rel. intensity) 268 ($M^+$+1, 100), 224 (40); $M_r$ (+CI) 268.118 35 [$M^+$+1] (calcd for $C_{13}H_{18}NO_5$ 268.118 49); Anal. ($C_{13}H_{17}NO_5 \cdot 0.25 H_2O$) C,H, N.

(c) Enriched (R)-2-N-(BENZYLOXYCARBONYL)AMINO-3-METHOXYPROPIONIC ACID (11)

Compound 10 (0.58 g) prepared hereinabove was dissolved in 80% aqueous methanol (3.0 mL). To this solution was added anhydrous $K_2CO_3$ (0.5 g) and the reaction mixture was stirred at room temperature (8 hours). The methanol was evaporated in vacuo and the residue suspended in water (50 mL). The aqueous suspension was washed with ethyl ether (2×25 mL) and then acidified to pH 3.0 using 5 N HCl. The acidified aqueous phase was extracted with ethyl acetate (3×25 mL). The ethyl acetate extracts were combined, dried ($Na_2SO_4$), filtered, and evaporated in vacuo to obtain pure 11 as a clear viscous oil (0.52 g, 95%): $R_f$ 0.30(10% $MeOH/CHCl_3$)

In a slight variation, the above compound was prepared as follows:

A mixture of enriched (R)-10(0.09 g, 0.33 mmol), MeOH (2.5 mL) and saturated aqueous $NaHCO_3$ (2.5 mL) was stirred at room temperature (24 hours) and then diluted with $H_2O$ (20 mL). The mixture was cooled (0° C.), acidified to pH 3.0 (5 N HCl) and extracted with EtOAc (3×25 mL). The EtOAc extracts were combined, dried (Na$_2$SO$_4$), filtered and evaporated in vacuo to obtain 11 (0.08 g, 98%) as a clear oil: [a] $^{23}{}_D$ (c=1.0, MeOH)=−3.2°; R$_f$ 0.30 (10% MeOH—CHCl$_3$) $^1$H NMR (CDCl$_3$) Δ 3.32 (s, OCH$_3$), 3.61 (dd, J=3.2, 9.3 Hz; CHH'OCH$_3$), 3.85 (dd, J=2.7, 9.3 Hz, CH H'OCH$_3$), 4.45–4.56 (m, CH), 5.11 (s, PhCH$_2$), 5.78 (d, J=8.4 Hz, NH), 7.28–7.47 (m, 5PhH); $^{13}$C NMR (CDCl$_3$) 54.2 (CH), 59.3 (OCH$_3$), 67.3 (PhCH$_2$), 72.2 (CH$_2$OCH$_3$), 128.1 (2C$_2$, or 2C$_3$,) 128.3 (C$_4$,), 128.6 (2C$_2$, or :2C$_3$,), 136.2 (C$_1$,), 156.5 (C(O)NH), 174 (C(O)OH) ppm; MS (+Cl) (rel. intensity) 254 (M$^+$+1, 35), 224(22), 210(27), 146(40), 118 (41), 113(32), 91(100); M$_r$ (+CI)254.103 28 [M$^+$+1] (calcd for C$_{12}$H$_{16}$NO$_5$ 254.102 84); Anal Calcd for C$_{12}$H$_{15}$NO$_5$·0.25 H$_2$): C, 55.92; H, 6.02; N, 5.44. Found: C, 56.08; H, 6.15; N, 5.24.

(d) Enriched (R)-N-BENZYL 2-(CARBOBENZYLOXYAMINO)-3-METHOXYPROPIONAMIDE (12)

A solution of 11 (0.52 g, 2.04 mmol) in dry tetrahydrofuran (10 mL) was cooled to −78° C. in a dry ice-acetone bath under a N$_2$ atmosphere. To this was added via a dry syringe 4-methylmorpholine (0.34 mL, 3.06 mmol). After stirring for 5 minutes, isobutyl chloroformate (0.4 mL, 3.06 mmol) was added via dry syringe and then the mixture stirred for 5 minutes. This was followed by the addition of benzylamine (0.32 mL, 3.06 mmol). After stirring at −78° C. for 5 minutes, the reaction was allowed to warm to room temperature, and stirring was continued at room temperature (30 min). The hydrochloride salt of 4-methyl morpholine was removed from the reaction by filtration. The clear filtrate was evaporated in vacuo and the residue was triturated with ethyl ether (5.0 mL). The white crystalline product obtained was isolated by filtration after washing with small amounts of ether and air-dried to give 12. (0.55 g, 78%): mp 112–114° C., R$_f$ 0.6 (10% MeOH/CHCl$_3$).

(e) Enriched (R)-N-BENZYL-2-AMINO-3-METHOXYPROPIONAMIDE(I)

To a solution of 12 (122.8 mg, 0.36 mmol) in methanol (2.0 mL) was added 10% Pd-C (11 mg) and the mixture stirred at room temperature in the presence of H$_2$ gas for 75 min. Celite was added to the reaction mixture and the catalyst was removed by filtration. The clear filtrate was evaporated in vacuo to give the compound of Formula I in the clear viscous oil (72 mg, 97%): R$_f$ 0.30 (5% MeOH/CHCl$_3$). The produce formed was an approximate 85:15 enantiomeric mixture of the R and S stereoisomers, respectively.

(f) Enriched (R)-N-BENZYL-2-ACETAMIDO-3-METHOXYPROPIONAMIDE(II)

To finish the synthesis in Scheme I, the following was performed. To a solution of I prepared hereinabove (0.20 g, 0.98 mmol) in dry THF (2.0 mL) is added pyridine (0.086 g, 1.08 mmol), and then acetic anhydride (0.2 g, 1.96 mmol) is added dropwise. The reaction is stirred at room temperature for 18 hours. The solvent is evaporated in vacuo and the residue purified by flash column chromatography to obtain the above compound. The compound formed was an approximate 85:15 enantiomeric mixture of the R and S stereoisomers, respectively.

EXAMPLE 2

Another method of preparing N-Benzyl 2-Amino 3-Methoxy Propionamide is depicted in Scheme 2 hereinabove and described in greater detail hereinbelow.

A. (R)-N-(BENZYLOXYCARBONYL) SERINE ((R)9).

Benzyl chloroformate (95%, 4.4 mL, 20.5 mmol) was added dropwise to a stirred aqueous (34 mL) mixture containing D-serine (1, 2.00 g, 19 mmol), MgO (2.40 g, 59.5 mmol) and Et$_2$O (16 mL) maintained at 0° C. After stirring (2 h), the mixture was allowed to warm to room temperature and stirring was continued (30 min). The mixture was filtered and the filtrate was washed with Et$_2$O (2×10 mL). The aqueous layer was cooled (0° C.) and the pH carefully adjusted to 3.0 using aqueous 5 N HCl. The acidified solution was stored in a refrigerator overnight and the white crystalline product 9 (2.24 g) isolated by filtration. The filtrate was extracted with EtOAc (2×20 mL) and the organic extracts were combined, dried (Na$_2$SO$_4$) filtered and evaporated in vacuo to obtain additional amounts of 9 (1.40 g). Total obtained upon drying in vacuo was 3.64 g (80%): mp 118–120° C. (lit. mp 119° C.); [α]$^{23}{}_D$ (c−5.6, glacial HOAc)=−5.5 (lit. [α]$^{23}{}_D$ (c=5.6, glacial HOAc)=−5.6°); $^1$H NMR (DMSO-d$_6$) Δ 3.32 (br s, OH), 3.62 (d, J=4.8 HZ, CHCH$_2$), 3.90–4.06 (m, CH), 5.01 (s, C(O)OCH$_2$), 7.20–7.40 (m, 5 PhH, NH).

B. (R)-N-BENZYL-2-N-(BENZYLOXYCARBONYL) AMINO-3-HYDROXYPROPIONAMIDE ((R)-13).

A dry THF solution (25 mL) containing (R)-9 (2.00 g, 8.4 mmol) was cooled (−78° C.) and then 4-methylmorpholine (1.4 mL, 10.5 mmol) was added. After stirring (2 min), isobutyl chloroformate (1.4 mL, 10.5 mmol) was added. The reaction was stirred (2 min) and then benzylamine (1.1 mL, 10.5 mmol) was added. The reaction was stirred at −78° C. (5 min), allowed to warm to room temperature and then stirred (1 h). The reaction mixture was filtered and the filtrate evaporated in vacuo. The residue was suspended in Et$_2$O (75 mL) and filtered. The crude product was purified by column chromatography (SiO$_2$, 10% MeOH—CHCl$_3$) to obtain 2.30 g (84%) of pure (R)-13 as a white solid: mp 147–149° C.; [α]$^{23}{}_D$ (c=2.0, MeOH)=+4.6°; R$_f$ 0.47 (10% MeOH—CHCl$_3$); IR (KBr) 3293, 1689, 1645, 1535, 1455, 1398, 1308, 1268, 1025, 754, 698 cm$^{-1}$; $^1$H NMR (DMSO-d$_6$) Δ 3.55–3.61 (m, CH$_2$OH), 4.05–4.10 (m, CH), 4.27 (d, J=5.7 Hz, NHCH$_2$), 4.89 (t, J=5.4 Hz, OH), 5.02 (s, CH$_2$OC(O)), 7.20–7.35 (m, 10 PhH, OC(O)NH), 8.40 (t, J=5.7 Hz, CON H); $^{13}$C NMR (DMSO-d$_6$) 42.1 (CH$_2$NH), 57.4 (CH), 61.8 (CH$_2$OH), 65.5 (OCH$_2$Ph), 126.7 (C$_4$' and C$_4$''), 127.0 (2C$_2$' or 2C$_3$' or 2C$_2$'' or 2C$_3$''), 127.8 (2C$_2$' or 2C$_3$' or 2C$_2$'' or 2 C$_3$''), 128.2 (2C$_2$' or 2C$_3$' or 2C$_2$'' or 2C$_3$''), 137.0 (C$_1$' or C$_1$'', 139.3 (C$_1$' or C$_1$''), 156.0 (C(O)O), 170.0 (C(O)NH) ppm; MS(+Cl) (rel intensity) 329 (M$^+$+1, 100), 285 (81), 221 (15), 286 (12); M$_r$ (+Cl) 329.150 20 [M$^+$+1] (calcd for C$_{18}$H$_{21}$N$_2$O$_4$ 329.150 13); Anal. (C$_{18}$H$_{20}$N$_2$O$_4$), C,H,N.

C. (R)-N-BENZYL-2-N-(BENZYLOXYCARBONYL) AMINO-3-METHOXYPROPIONAMIDE ((R)-14).

To a CH$_3$CN solution (50 mL) of (R)-13 (1.60 g, 4.9 mmol) was successively added Ag$_2$O (7.20 g, 24.4 mmol) and MeI (4.0 mL, 49 mmol) at room temperature, and then the reaction mixture was stirred at room temperature (3 days). The insoluble salts were filtered and the solvent was evaporated in vacuo. The residue was purified by column chromatography (SiO$_2$, 5% MeOH—CHCl$_3$) to obtain (R)-14 as a white crystalline solid (1.40 g, 84%): mp 128–130° C.; [α]$^{23}{}_D$ (c=1.1., MeOH)=+2.80; R$_f$ 0.77 (10% MeOH—CHCl$_3$; IR (KBr) 3294, 2880, 1688, 1641, 1534, 1458, 1397, 1314, 1233, 1128, 1954, 964, 755, 699 cm$^{-1}$; $^1$H NMR (CDCl$_3$) Δ 3.37 (s, OCH$_3$), 3.50 (dd, J=2.7, 9.3 Hz, C HH'OCH$_3$), 3.87 (dd, J=3.9, 9.3 Hz, CHH'OCH$_3$), 4.35–4.40 (m, CH), 4.49 (d, J=6.0 Hz, NHCH$_2$), 5.13 (s, C(C)OCH$_2$) 5.65–5.75 (m, NH) 6.67–6.70 (m, NH), 7.22–7.45 (m, 10 Ph H); $^{13}$C NMR (CDCl$_3$) 43.7 (CH$_2$NH), 54.5 (CH), 59.3 (OCH$_3$), 67.4 (C(O)OCH$_2$), 72.2 (CH$_2$OCH$_3$), 127.6 (C$_4$' and C$_4$"), 128.3 (2C$_2$' or 2C$_3$' or 2C$_2$" or 2C$_3$"), 128.5 (2C$_2$' or 2C$_3$' or 2C$_2$" or 2C$_3$"), 128.8 (2C$_2$" or 2C$_3$' or 2C$_2$" or 2C$_3$"), 128.9 (2C$_2$' or 2C$_3$' or 2C$_2$" or 2C$_3$), 136.2 (C$_1$' or C$_1$"), 138.0 (C$_1$' or C$_1$"), 156.3 (C(O)O), 170.0 (C(O)NH) ppm; MS (+Cl) (rel. intensity) 343 (M$^+$+1, 100), 299 (40), 235 (31); M$_r$ (+Cl) 343.166 81 [M$^+$+1] (calcd for C$_{19}$H$_{23}$N$_2$O$_4$ 343.165 78); Anal. (C$_{19}$H$_{22}$N$_2$O$_4$·0.25H$_2$O) C, H, N.

D. (R)-N-BENZYL-2-AMINO-3-METHOXYPROPIONAMIDE (I).

A MeOH (50 mL) solution of (R)-14 (1.00 g, 2.9 mmol) was hydrogenated in the presence of 10% Pd-C (0.20 g) at room temperature (3h). The mixture was filtered through Celite and the clear filtrate was evaporated in vacuo to obtain a pale yellow oil which O was purified by column chromatography (SiO$_2$, 10% MeOH—CHCl$_3$) to obtain the compound of Formula I as the R isomer (0.61 g, 100%) as a pale yellow oil: $[\alpha]^{23}_D$ (c=1.5, MeOH)=–2.0°; R$_f$ 0.34 (10% MeOH—CHCl$_3$); IR (liquid film) 3352, 3311, 3064, 2927, 2826, 1655, 1527, 1455, 1360, 1251, 1181, 1106, 971, 734, 700 cm$^{-1}$; $^1$H NMR (CDCl$_3$) Δ 1.85 (br s, NH$_2$), 3.34 (s, OCH$_3$), 3.56–3.62 (m, CHOCH$_2$), 4.39 (dd, J=6.0 15.2 Hz, NHCHH') 4.45 (dd, J=6.0, 15.2 Hz, NHCHH'), 7.20–7.36 (m, 10 PhH), 7.80–7.88 (m, NH); $^{13}$C NMR (CDCl$_3$) 43.1 (NHCH$_2$) 54.9 (CH), 58.9 (OCH$_3$), 74.6 (CH$_2$OCH$_3$), 127.4 (C$_4$') 127.6 (2C$_2$' or 2C$_3$'), 128.6 (2C$_2$' or 2C$_3$'), 138.4 (C$_1$') 172.8 (C(O)) ppm; MS (+Cl) 209 (M$^+$+1) ; M$_r$ (+Cl) 209.129 19 [M$^+$+1] calcd for C$_{11}$H$_{17}$N$_2$O$_2$ 209.129 00); Anal. (C$_{11}$H$_{16}$N$_2$O$_2$·0.15 H$_2$O) C,H,N.

E. (R)-N-BENZYL-2-ACETAMIDO-3-METHOXYPROPIONAMIDE((R)-II).

Determination of the Enantiomeric Purity of (R)-I.

To a solution of the compound of Formula I prepared in Part D hereinabove (0.06 g, 0.3 mmol) in dry THF (3 mL) was added successively pyridine (0.02 mL, 0.3 mmol), DMAP (~0.005 g), and Ac$_2$O (0.03 mL, 0.3 mmol), and the resulting solution was stirred at room temperature (1 hour). The solvents were evaporated in vacuo and the residue was purified by PTLC (SiO$_2$, 5% MeOH—CHCl$_3$) to obtain a compound of Formula II as the R stereoisomer (0.07 g, 90%) as a white solid: mp 142–143° C.; $[\alpha]^{23}_D$ (c=1, MeOH)=+16.2°; R$_f$ 0.47 (10% MeOH—CHCl$_3$); $^1$H NMR (CDCl$_3$) Δ 2.05 (s, C(O)CH$_3$), 3.39 (s, OCH$_3$) 3.45 (dd, J=7.8, 9.0 Hz, CHH'OCH$_3$), 3.83 (dd, J=4.2, 9.0 Hz, CHH'OCH$_3$), 4.49 (d, J=5.7 Hz, NHCH$_2$); 4.53–4.59 (m, CH), 6.40–6.51 (m, NH), 6.77 (br s, NH), 7.26–7.42 (m, 5 PhH).

Addition of excess (R)-(-)-mandelic acid to a CDCl$_3$ solution of (R)-II gave only one signal for the acetyl methyl and ether methyl protons, thereby indicating that the compound of Formula R-I, as prepared herein was substantially enantiomerically pure, as defined herein.

The compound of the present invention exhibits anti-convulsant activity, as indicated hereinbelow.

PHARMACOLOGY

Compounds were screened for anticonvulsant activity in both male albino Carthworth Farms No. 1 mice (ip route) and male albino Sprague Dawley rats [oral (po) route]. Activity was established using the electrical (maximal electroshock or MES) test. In the MES test, a drop of electrolyte solution with anesthetic (0.5% butacaine hemisulfate in 0.9% sodium chloride) was used in the eyes of the animals prior to positioning the corneal electrodes and delivery of current. A 60 cycle alternating current was administered for 0.2 sec. in both species, 50 mA in mice and 150 mA in rats. Protection endpoints were defined as the abolition of the hind limb tonic extensor component of the induced seizure. In mice, effects of compounds on forced spontaneous motor activity were determined using the rotorod test. The inability of animals to maintain their balance for 1 min. on a 1 inch diameter knurled rod at 6 rpms in 3 successive trials demonstrated motor impairment. Normally under these conditions, mice maintain their balance almost indefinitely. In rats, motor impairment is assessed by observing for overt evidence of ataxia, abnormal gait and stance, and/or loss of placing response and muscle tone. In the mouse identification screening study all compounds were given at three dose levels (30, 100, 300 mg/kg) and two time periods (0.5 hours, 4 hours). Typically, in the MES seizures test one animal was tested at 30 mg/kg and 300 mg/kg, and three animals at 100 mg/kg. In the rotorod toxicity test four animals were tested at 30 mg/kg, and 300 mg/kg, and eight animals at 100 mg/Kg. If activity was found at 30 mg/Kg, then lower dosages were used to find the ED$_{50}$ values.

The quantitative determination of the median effective (ED$_{50}$) and toxic doses (TD$_{50}$) was conducted at previously calculated times of peak effect. Groups of at least eight animals were tested using different doses of test compound until at least two points were determined between 100 and 0% protection and minimal motor impairment. The dose of candidate substance required to produce the defined end-point in 50% of the animals in each test and the 95% confidence interval was calculated.

The compound of the present invention as well as standard anti-convulsant drugs were each subjected to the tests indicated hereinabove.

The results are tabulated hereinbelow.

TABLE

ANTICONVULSANT ACTIVITY OF I AND KNOWN ANTI-EPILEPTIC DRUGS

| Compound | MES ED$_{50}$$^a$(mg/kg) | TOX TD$_{50}$$^b$(mg/kg) |
|---|---|---|
| CH$_2$OCH$_3$<br>\|<br>H$_2$N—CHCNHCH$_2$Ph<br>\|\|<br>O<br>(R) | >30, <100 (ip)<br>18 (po) | >100, <300 (ip)<br>>500 (po) |
| phenytoin | 6.5 (ip)<br>23.2 (po) | 43 (ip)<br>>500 (po) |
| carbamazepine | 9.9 (ip)<br>3.8 (po) | 47.8 (ip)<br>361 (po) |
| valproic acid | 287 (ip)<br>395 (po) | 483 (ip)<br>859 (po) |

$^a$Maximal electroshock seizure test, ip studies conducted in mice, oral studies in rats.
$^b$Neurological toxicity (minimal motor impairment).

As clearly shown by the above data, the R isomer exhibits anticonvulsant activity, however, it is noted that the activity in the rat model was greater than in the mouse model.

In addition, the compound of the present invention has relatively low neurological toxicity. In fact, as clearly shown by the data, the neurological toxicity is significantly lower in rats in which the compounds were administered orally than in the mice in which the compounds were administered intraperitoneally. In fact, in rats, the neurological toxicity of the R isomer of the compound of the present invention is very low.

The above preferred embodiments and examples are given to illustrate the scope and spirit of the present inven-

What is claimed is:

1. A compound of the formula:

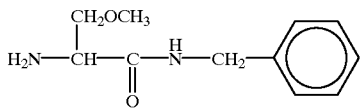

or pharmaceutically acceptable salts thereof.

2. The compound of claim 1 which is in the R configuration.

3. A substantially pure compound of claim 1.

4. A substantially pure compound of claim 2.

5. The compound of claim 2 which is substantially enantiopure.

6. A pharmaceutical composition comprising an anti-convulsant effective amount of the compound according to claim 1 and a pharmaceutical carrier therefor.

7. The pharmaceutical composition according to claim 6 wherein said compound is in the R-configuration.

8. The pharmaceutical composition according to claim 6 wherein said compound is substantially pure.

9. The pharmaceutical composition according to claim 7 wherein said compound is substantially pure.

10. The pharmaceutical composition according to claim 7 wherein the compound is substantially enantiopure.

11. A method of treating central nervous system disorders in an animal comprising administering to said animal in need thereof an anti-convulsant effective amount of a compound according to claim 1.

12. The method according to claim 11 wherein the compound is in the R configuration.

13. The method according to claim 11 wherein the animal is a mammal.

14. The method according to claim 13 wherein the mammal is human.

15. The method according to claim 12 wherein the animal is a mammal.

16. The method according to claim 15 wherein the mammal is human.

17. The method according to claim 11 wherein the compound is substantially pure.

18. The method according tc claim 12 wherein the compound is substantially pure.

19. The method according to claim 12 wherein the compound is substantially enantiopure.

* * * * *

UNITED STATES PATENT AND TRADEMARK OFFICE
CERTIFICATE OF CORRECTION

PATENT NO. : 6,048,899
DATED : April 11, 2000
INVENTOR(S) : Harold Kohn, et al.

It is certified that error appears in the above-identified patent and that said Letters Patent is hereby corrected as shown below:

Column 1, Line 10: Insert

--This invention was made with Government support under Grant No.

NIH-NS 15604 awarded by the National Institute of Health. The Government has certain rights in the invention.--

Column 3, Line 35: "T1" should read --II--

Column 10, Line 8: "42" should read --2--

Column 10, Line 35: "Jx3.3" should read --J=3.3--

Column 11, Line 4: "$\Delta$" should read --$\delta$--

Column 11, Line 9: ":2" should read --2--

Column 12, Line 19: "$\Delta$" should read --$\delta$--

Column 12, Line 38: "$\Delta$" should read --$\delta$--

Column 12, Line 64: "$\Delta$" should read --$\delta$--

UNITED STATES PATENT AND TRADEMARK OFFICE
CERTIFICATE OF CORRECTION

PATENT NO. : 6,048,899
DATED : April 11, 2000
INVENTOR(S) : Harold Kohn, et al.

It is certified that error appears in the above-identified patent and that said Letters Patent is hereby corrected as shown below:

Column 13, Line 16: Delete --O--

Column 13, Line 22: " Δ." should read --δ--

Column 13, Line 44: "Δ" should read --δ--

Column 16, Line 22, Claim 18: "tc" should read --to--

Signed and Sealed this

Twenty-seventh Day of March, 2001

NICHOLAS P. GODICI

Attest:

Attesting Officer

Acting Director of the United States Patent and Trademark Office